United States Patent
Vasquez

(10) Patent No.: US 10,209,392 B2
(45) Date of Patent: Feb. 19, 2019

(54) METHOD AND SYSTEM FOR MONITORING FOR SCALE

(71) Applicant: Halliburton Energy Services, Inc., Houston, TX (US)

(72) Inventor: Quintilio Vasquez, Al Khobar (SA)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/226,740

(22) Filed: Aug. 2, 2016

(65) Prior Publication Data

US 2018/0038989 A1 Feb. 8, 2018

(51) Int. Cl.
*G01N 23/222* (2006.01)
*G01V 5/10* (2006.01)
*E21B 49/00* (2006.01)

(52) U.S. Cl.
CPC .............. *G01V 5/101* (2013.01); *E21B 49/00* (2013.01); *G01N 23/222* (2013.01)

(58) Field of Classification Search
CPC ..................................................... G01N 33/20
See application file for complete search history.

(56) References Cited

U.S. PATENT DOCUMENTS

| | | | | | |
|---|---|---|---|---|---|
| 2,691,109 | A | * | 10/1954 | Bernard | G01V 5/06 250/260 |
| 2,772,951 | A | * | 12/1956 | Bond | E21B 49/005 436/111 |
| 4,357,143 | A | * | 11/1982 | Scott | G01N 30/96 204/409 |
| 4,472,354 | A | * | 9/1984 | Passell | G01N 30/88 210/298 |
| 4,712,424 | A | * | 12/1987 | Herron | G01V 11/00 250/256 |
| 4,722,220 | A | * | 2/1988 | Herron | G01V 11/00 250/253 |
| 4,779,679 | A | * | 10/1988 | Snavely, Jr. | C09K 8/528 166/279 |
| 4,807,469 | A | * | 2/1989 | Hall | E21B 21/08 175/42 |
| 4,856,584 | A | * | 8/1989 | Seidner | E21B 41/02 166/250.05 |
| 4,903,527 | A | * | 2/1990 | Herron | G01V 11/00 702/12 |

(Continued)

FOREIGN PATENT DOCUMENTS

WO 2016007117 A1 1/2016

OTHER PUBLICATIONS

Mike Crabtree et al., Fighting Scale-Removal and Prevention, Oil Field Review, 1999, 16 pages.

(Continued)

*Primary Examiner* — David Porta
*Assistant Examiner* — Djura Malevic
(74) *Attorney, Agent, or Firm* — Chamberlain Hrdlicka

(57) ABSTRACT

A method and system of monitoring for scale compounds that include scale co-contributors of cations and anions. A scale compound can be monitored by measuring gamma ray counts of scale contributors using a spectral gamma ray detector. A scale compound can be identified by identifying an increase in scale co-contributors over time from the gamma ray counts.

20 Claims, 7 Drawing Sheets

(56) References Cited

U.S. PATENT DOCUMENTS

| | | | | |
|---|---|---|---|---|
| 4,904,603 | A * | 2/1990 | Jones | E21B 49/005 175/42 |
| 5,005,406 | A * | 4/1991 | Jasinski | E21B 47/102 324/370 |
| 6,777,669 | B2 * | 8/2004 | Fitzgerald | G01V 5/04 250/256 |
| 6,792,796 | B2 * | 9/2004 | Hammonds | E21B 37/06 166/250.05 |
| 6,880,402 | B1 * | 4/2005 | Couet | B08B 3/12 73/1.49 |
| 8,510,050 | B2 | 8/2013 | Truax et al. | |
| 8,936,430 | B2 | 1/2015 | Bassett | |
| 9,249,654 | B2 * | 2/2016 | Strachan | E21B 44/00 |
| 2002/0070337 | A1 * | 6/2002 | Fitzgerald | G01V 5/04 250/256 |
| 2007/0284108 | A1 * | 12/2007 | Roes | E21B 36/04 166/302 |
| 2014/0330520 | A1 | 11/2014 | Kwong | |
| 2015/0198037 | A1 * | 7/2015 | Van Hal | G01N 33/20 73/152.42 |
| 2017/0108611 | A1 * | 4/2017 | Vasquez | G01V 5/105 |

OTHER PUBLICATIONS

Halliburton, Reservoir Monitor Tool, Cased-Hole Formation Evaluation, 2004, 4 pages.

Scale Problems in Production, Society of Petroleum Engineers (SPE International), (http://petrowiki.org/Scale_problems_in_production), dated Jan. 19, 2016, 7 pages.

ESP Optional Components, Society of Petroleum Engineers (SPE International), (http://petrowiki.org/ESP_optional_components), dated Jan. 19, 2016, 5 pages.

P.E. Fox, G. Adnyiana, and I. Setiadi; Applications of Carbon/Oxygen Logging in Indonesian Reservoirs; SPE 54353; Presentation for the 1999 SPE Asia Pacific Oil and Gas Conference and Exhibition held in Jakarta, Indonesia, Apr. 20-22, 1999, 16 Pages.

L.A. Jacobson, R. Ethridge, and G. Simpson; A New Small-Diameter High-Performance Reservoir Monitoring Tool; SPWLA 39th Annual Logging Symposium, May 26-29, 1998; 14 Pages.

Jerome A. Truax, Larry A. Jacobson, Gary A. Simpson, Dennis P. Durbin, and Quintilio Vasquez; Field Experience and Results Obtained with an Improved Carbon/Oxygen Logging System for Reservoir Optimization; SPWLA 42 Ad Annual Logging Symposium, Jun. 17-20, 2001; 14 pages.

* cited by examiner

METHOD AND SYSTEM FOR MONITORING FOR SCALE

BACKGROUND

This section is intended to provide background information to facilitate a better understanding of the various aspects of the described embodiments. Accordingly, it should be understood that these statements are to be read in this light and not as admissions of prior art.

Many waters contain alkaline earth metal cations, such as barium, strontium, calcium, magnesium, and anions, such as sulfate, bicarbonate, carbonate, phosphate and fluoride. Precipitates can form when combinations of these anions and cations are present in concentrations which exceed the solubility product of a scale compound. For example, when the concentrations of barium and sulfate ions exceed the solubility product of barium sulfate, a solid phase of barium sulfate will form as a precipitate. Solubility products are exceeded for various reasons, such as evaporation of the water phase; changes in the pH, pressure, or temperature; and the introduction of additional ions which can form insoluble compounds with the ions already present in the solution.

As these reaction products precipitate on surfaces of water-carrying or water-containing systems, they form adherent deposits or scale. Scale can interfere with fluid flow, particularly in production systems for oil and gas. As an example, when formation fluid with brine is brought to the surface, scale can deposit inside production pipe and downhole tools, such as submersible pumps, constricting the production flow.

BRIEF DESCRIPTION OF THE DRAWINGS

For a detailed description of the embodiments of the invention, reference will now be made to the accompanying drawings in which.

DETAILED DESCRIPTION

Figure 1:
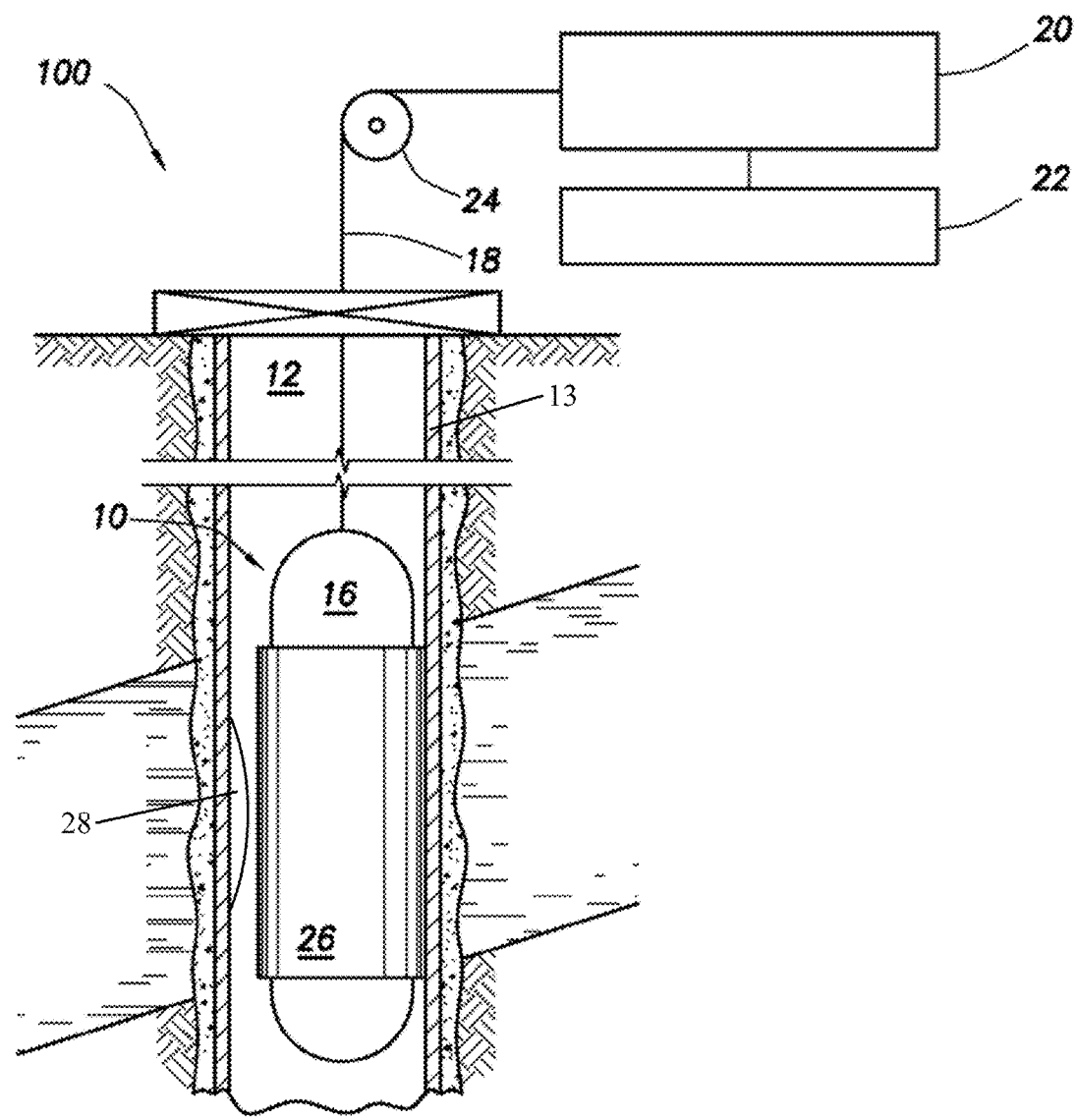
FIG. 1 depicts a schematic view of an example nuclear logging system for monitoring for a scale compound on equipment, according to one or more embodiments.

This disclosure provides a method of monitoring scale downhole. Specifically, the scale deposits can be monitored by deploying gamma ray detectors in a borehole intersecting a subterranean earth formation to obtain elemental concentrations of scale contributors (i.e., an element of an anion or cation in a scale compound). These concentrations can be monitored over time to identify and quantify scale deposit development and determine when and which scale removal process is suitable for remediating the scale deposit.

Changes in pressure, temperature, or acidity of formation fluid from an earth formation, as it is brought to the surface, can contribute to scale deposits forming in a borehole, such as on borehole casing, drill string, coiled tubing, production string, an electric submersible pumps (ESPs) installed along the production string, completion equipment, formation evaluation equipment, valves, or any other suitable tubular or tool located in a borehole. To increase hydrocarbon production, water can be injected in a hydrocarbon reservoir (i.e., waterflooding). The mixing of seawater, which is rich in sulphate and used in waterflooding, with formation water, which is rich in brine, increases the scaling tendency. Seawater injected into oil or gas containing formations disturbs the chemical equilibriums in the formation fluid leading to the precipitation of carbonate or sulphate scales. During the production process, formation fluids with brine can mix with scale contributors, precipitating on the production string or downhole tools as scale. For example, occasionally, ESPs are used in a wellbore to drive hydrocarbon fluids to the surface. In water-flooded or brine-rich hydrocarbon reservoirs, scale deposits can form in ESPs under conditions conducive to precipitation such as changes in pressure, temperature, or acidity, and can hinder the pumping capacity of the ESP.

Some currently-existing methods of monitoring scale deposits in a borehole can be unreliable or costly. For example, temperature logs provide a continuous temperature profile of a borehole. A disturbance in the temperature profile at a location in the borehole might indicate scale deposits forming in the borehole. However, other factors can contribute to disturbances in temperature in the well, thus leading to an inaccurate indicator of scale deposits. Total gamma ray tools can identify increases in gamma ray counts, which might indicate increases in scale deposits, but these logs can lead to misinterpretation from uranium salts in the production fluid. Another option is to stop production, remove the tubing or downhole tool, and check if there are scale deposits. However, it is costly to check for scale by removing the tubing or downhole tool, because production is stopped regardless of whether and to what extent scale deposits are on the tubing or downhole tool.

An efficient and accurate method of monitoring for scale deposits is to recover gamma ray logs that indicate the elemental concentrations of potential scale contributors. As described herein, a scale contributor refers to an element of an anion or cation in a scale compound, and scale co-contributors refer to the scale contributors in the same scale compound. Examples of classes of scales in hydrocarbon and water fields include sulphates, carbonates, iron oxides, iron sulfides, and salts. The scales most often encountered in hydrocarbon facilities are carbonates and sulphates. Common scale compounds that may be present in hydrocarbon and water fields include magnetite ($Fe_3O_4$), iron oxide ($Fe_2O_3$), pyrite ($FeS_2$), marcasite ($FeS_2$), pyrrhotite ($Fe_xS$), troilite (FeS), siderite ($FeCO_3$), calcite ($CaCO_3$), anhydrate ($CaSO_4$), celestite ($SrSO_4$), radium sulfate ($RaSO_4$), barite ($BaSO_4$), and halite (NaCl).

Naturally occurring radioactive materials (NORM) such as radium can be a scale contributor. Radium (Ra) is chemically similar to barium (Ba), calcium (Ca), and strontium (Sr). That is, radium nuclides tend to co-precipitate with alkaline earth carbonates or sulphates (e.g., $CaCO_3$, $SrSO_4$, $BaSO_4$), replacing calcium, barium, or strontium cations in the crystal structures, and forming radium sulphate, radium carbonate, and (in some cases) radium silicate.

A nuclear logging tool including a high density gamma ray detector can be deployed in a borehole intersecting a subterranean earth formation to monitor potential scale deposits. Gamma ray information can indicate the concentrations of naturally occurring radioactive scale contributors, such as radium (Ra), and, with a neutron source, nuclear activated scale contributors, such as calcium (Ca), iron (Fe), oxygen (O), or sulfur (S).

FIG. 1 depicts a schematic view of a nuclear logging system 100 employed in a borehole 12, in accordance with one or more embodiments. As shown, the system 100 comprises a logging tool 10 placed within the borehole 12. The borehole 12 may have a casing 13, as depicted in FIG. 1, or it may be uncased or open hole.

The tool 10 comprises a pressure vessel 16 within which various subsystems of the tool 10 reside, and in the illustrative case of FIG. 1 the pressure vessel 16 is suspended within the borehole 12 by a cable 18 such that the tool is run through a portion of the interior of the casing 13. The cable 18 may include, without limitation, a wireline cable, a slickline cable, coiled tubing, etc. The cable 18 communicatively couples the tool 10 to a telemetry module 20 and a surface control unit 22, such as a processor and a suitable display medium. The processor of the surface control unit 22 can be configured to perform one or more methods as described herein. For example, the processor may analyze the logging data generated by the tool 10 as further described herein.

The tool 10 may be raised and lowered within the borehole 12 by way of the cable 18, and the depth of the tool 10 within the borehole 12 may be determined by depth measurement system 24 (illustrated as a depth wheel). In some embodiments, the pressure vessel 16 may be covered with a thermal neutron absorptive material 26 (the thickness of which is exaggerated for clarity in the figure). However, in other embodiments the material 26 may be only partially present or may be omitted altogether.

The tool 10 may be used to monitor for scale 28 depositing in the borehole 12, such as scale 28 forming on the casing 13, as further described herein. The tool 10 may include a pulsed neutron logging tool and used in conjunction with data analysis software. An example method used by the tool 10 for monitoring for scale 28 may include, neutron induced gamma ray spectroscopy and/or passive gamma ray spectroscopy. A commercial example of a suitable tool 10 is the RMT Elite™ Reservoir Monitor Tool available from Halliburton Energy Services, Inc., Houston, Tex.

Figure 2:
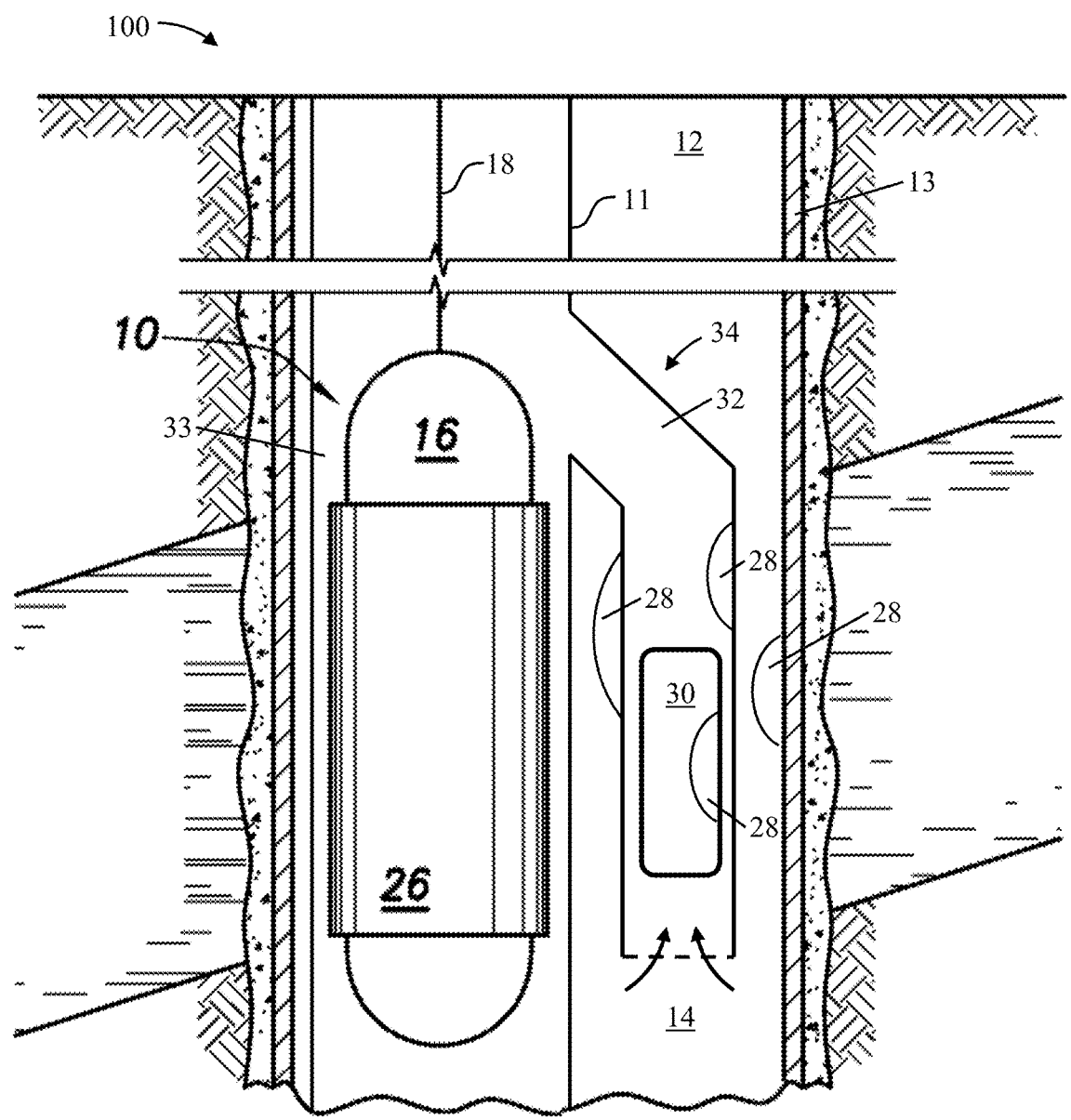
FIG. 2 depicts a schematic view of the nuclear logging system of FIG. 1, according to one or more embodiments.

FIG. 2 depicts a schematic view of the nuclear logging system 100 used to monitor for scale compounds forming in a production string 11, in accordance with one or more embodiments. As shown, the tool 10 is deployed in the production string 11 proximate to a pump 30 (e.g., an ESP) installed in a production branch 32 of a Y-tool 34. The tool 10 is run into the bypass string 33 of the Y-tool 34 and used to measure gamma ray spectral energy signatures of scale contributors associated with potential scale compounds depositing on or in the pump as further described herein. For example, as the pump 30 transfers formation fluid 14 into the production string 11, the pump 30 produces fluctuations in temperature, pressure, or pH of the formation fluid 14, which allows scale 28 to precipitate and deposit on or in the pump 30, Y-tool 33, or on the casing 13, thus, reducing the capacity of the pump 30 to deliver formation fluid 14 to the surface.

It should be appreciated that monitoring for scale is not limited to monitoring for scale forming on or in a pump installed in a well. Scale may form in or in the Y-tool 40, borehole 12, casing 13, production string 11, perforations through the casing and formation, surface equipment, etc. The tool 10 may be used to monitor for scale depositing on these as well as the pump or as an alternative. Thus, the tool 10 may be used to monitor for scale forming on any equipment in contact with scale contributors, and not necessarily used downhole. For example, alternative equipment undergoing scale monitoring may include completion equipment (such as packers), formation evaluation equipment (such as gravimeters, seismic sensors, resistivity tools, nuclear logging tools, nuclear magnetic resonant tools, or any other suitable formation evaluation tool), valves, surface pumps, tubing, or any other suitable tool on or in which scale may deposit. The tool 10 may be used to monitor for scale through a structure, such as through the production string 11, Y-tool 40, or pump 30.

Figure 3:
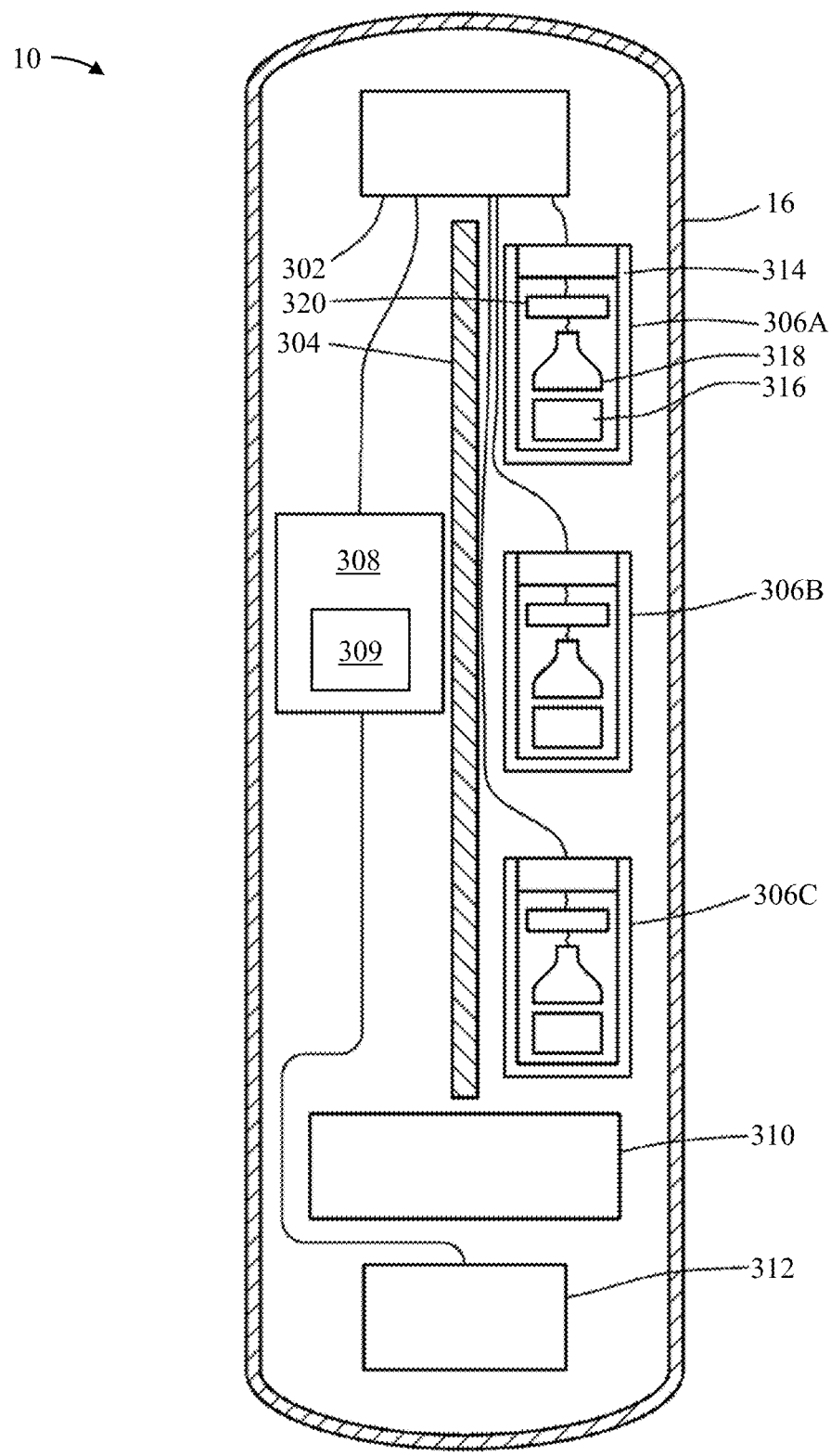
FIG. 3 depicts a schematic of the example nuclear logging tool of FIG. 1, according to one or more embodiments.

FIG. 3 shows a schematic view of the nuclear logging tool 10 of FIGS. 1 and 2 in accordance with one or more embodiments. As shown, the pressure vessel 16 houses various components, such as a telemetry module 302, a borehole shield 304, spectral gamma ray detectors 306A-C, a control module 308, a neutron shield 310, and a neutron source 312. The control module 308 includes a processor 309 configured to perform one or more methods as described herein.

While the gamma ray detectors 306A-C are shown above the neutron source 312, in other embodiments the gamma ray detectors may be below the neutron source. Gamma ray detector 306C may be about 12 inches (30.5 cm) from the neutron source 312. The gamma ray detector 306B may be about 24 inches (61 cm) from the neutron source 312; and the gamma ray detector 306A may about 32.5 to 36 inches (82.5-91.4 cm) from the neutron source 312. Alternatively, the gamma ray detectors 306A-C may be separated based on other suitable spacings.

The neutron source 312 includes one or more neutron generators capable of producing and/or releasing neutrons with at least 8 Mega-Electron Volts (MeV). The neutron source 312, under command from the surface control unit 22 in the case of wireline tools, or control module 308 within the tool in the case of slickline tools, generates and/or releases energetic neutrons. To reduce the irradiation of the gamma ray detectors 306A-C and other devices by energetic neutrons from the neutron source 312, the neutron shield 310 separates the neutron source 203 from the gamma ray detectors 207A, 207B. The neutron shield 310 can include boron carbide or any other suitable material that absorbs neutrons and produces virtually no gamma radiation.

The shield 304 is interposed between the gamma ray detectors 306A-C and materials that produce gamma rays from neutron collision or interaction (such as ferrous materials in the casing 13 or borehole 12 (FIG. 1)). The shield 304 may absorb gamma rays emitting from an orientation or direction that is not being monitored for scale, thus, improving the gamma ray spectroscopy of the scale monitored. The shield 304 may include a high density material, such as lead, depleted uranium, or any other material suitable for absorbing gamma rays.

Because of the speed of the energetic neutrons (e.g., 30,000 kilometers/second or more), and because of collisions of the neutrons with atomic nuclei that change the direction of movement of the neutrons, a neutron flux is created around the nuclear logging tool 10 that can surround and/or extend into materials proximate the tool 10 undergoing scale monitoring, e.g., the pump 30, production string 11, casing 13, etc. Neutrons generated and/or released by the source 312 interact with atoms by way of inelastic collisions and/or thermal capture.

In the case of inelastic collisions, a neutron inelastically collides with atomic nuclei, a gamma ray is created (an inelastic gamma ray), and the energy of the neutron is reduced. The neutron may have many inelastic collisions with the atomic nuclei, each time creating an inelastic gamma ray and losing energy. At least some of the gamma rays created by the inelastic collisions are incident upon the gamma ray detectors 306A-C. The arrival time of a particular gamma ray, its energy, or both may be used to determine its status as an inelastic gamma ray.

After one or more inelastic collisions (and corresponding loss of energy), a neutron reaches an energy known as thermal energy (i.e., a thermal neutron). A neutron at thermal energy can be captured by atomic nuclei. In a capture event, the capturing atomic nucleus enters an excited state and the nucleus later transitions to a lower energy state by release of energy in the form of a gamma ray (known as a thermal gamma ray). At least some of the thermal gamma rays created by thermal capture are also incident upon the gamma ray detectors 306A-C and the arrival time of a particular gamma ray, its energy, or both may be used to determine its status as a capture gamma ray. Only inelastic and thermal capture interactions produce gamma rays.

Referring to FIG. 3, when operational, the gamma ray detectors 306A-C detect arrival and energy of gamma rays, including gamma rays emitted by a scale contributor, e.g., a scale contributor on or in the pump 30 of FIG. 2. The gamma ray detectors 306A-C may be spectral gamma ray detectors configured to generate energy spectra measurements for elements and/or a normalized energy spectrum. Although this discussion is directed to the gamma ray detector 306A, it is applicable to the scope of gamma ray detectors 306B and C as well. The gamma ray detector 306A comprises an enclosure 314, and within the enclosure 314 resides a scintillator crystal 316, a photomultiplier tube 318 optically coupled to the crystal 316, and a processor 320 coupled to the photomultiplier tube 318.

As gamma rays are incident upon or within the crystal 316, the gamma rays interact with the crystal 316 and flashes of light are emitted. Each flash of light itself is indicative of an arrival of a gamma ray, and the intensity of light is indicative of the energy of the gamma ray.

The output of the photomultiplier tube 318 is proportional to the intensity of the light associated with each gamma ray arrival at the crystal 316, and control module 308 can quantify the output as gamma ray measurements indicative of the gamma energy and relays the information to the surface control unit 22 (FIG. 2) by way of telemetry signals in the case of wireline tools, or stores the information within the tool in the case of slickline tools. As used herein, gamma ray measurements refer to gamma ray counts and/or gamma ray count rates produced by at least one of the gamma ray detectors 306A-C. As used herein, gamma ray measurements of a scale contributor refers to measurements indicative of gamma rays emitted from that scale contributor.

Figure 4:
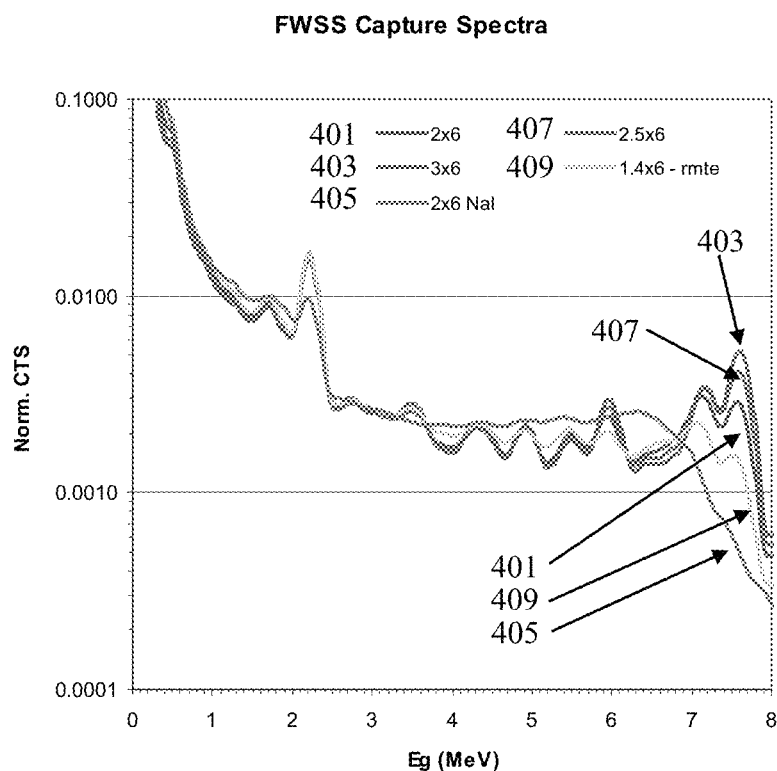
FIG. 4 depicts a graph view of gamma ray energy spectra, according to one or more embodiments.
Figure 5:
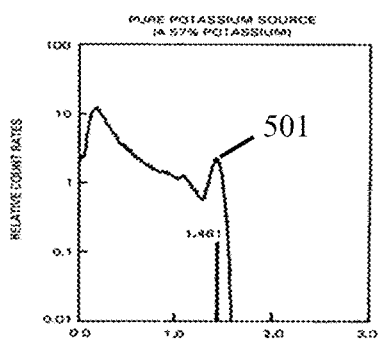
FIGS. 5-8 depict graph views of relative gamma ray spectra, according to one or more embodiments.
Figure 6:
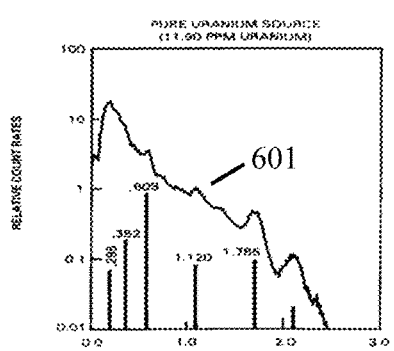
Figure 7:
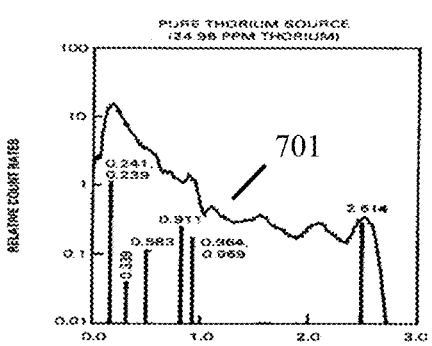
Figure 8:
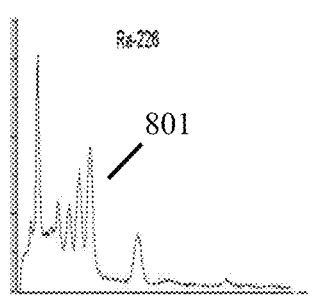

FIG. 4 depicts a graph view of energy spectra for various dimensions and densities of spectral gamma ray detectors in accordance with one or more embodiments. Each crystal has a six inch length but a different diameter or density. A curve 401 is shown and represents an energy spectrum produced by a crystal with a two inch diameter; a curve 403 is shown and represents an energy spectrum produced by a crystal with a three inch diameter; a curve 405 is an energy spectrum for a NaI crystal with a two inch diameter; a curve 407 is an energy spectrum for a crystal with a 2.5 inch diameter; and a curve 409 is an energy spectrum for a crystal with a 1.4 inch diameter. The curve 405 demonstrates that the NaI crystal does not have enough mass to provide an energy spectrum that can be used to identify individual scale contributors.

The crystal 316 may be selected with a mass sufficient to determine individual elemental concentrations of scale contributors, such as calcium, sulfur, iron, oxygen, or radium. The crystal 316 may be configured to be responsive to gamma rays emitted from scale contributors. The crystal 316 may have a mass of at least 900 grams and a gamma stopping power of at least 11. As an example, the crystal 316 may include a gamma ray responsive material, such as bismuth germanate (BGO), having a diameter of about 1.4 inches (3.6 cm) and length of about 6 inches (15 cm).

FIGS. 5-8 depict graph views of relative gamma ray count rates showing basis spectra (pure element spectra) curves for potassium 501, uranium 601, thorium 701, and radium 801, according to one or more embodiments. The energy spectrum captured by the gamma ray detectors 306A-C (e.g., curve 409 of FIG. 3) is corrected for natural radionuclides and background radiation (e.g., irradiated casing 13, pressure vessel 16, or other ferrous materials) by subtracting a fraction of this background spectrum from the captured spectrum. The corrected spectrum is divided into multiple energy windows and the gamma ray count rates in these energy windows are fit with basis spectra (for example, but not limited to the basis curves depicted in FIGS. 5-8) through computer modeling. For example, the modeling may use a weighted least-squares fitting procedure (or any other suitable regression method) to determine the relative contributions of each of the basis spectra or scale contributors (for example, but not limited to, calcium, sulfur, iron, oxygen, and radium).

Figure 9:
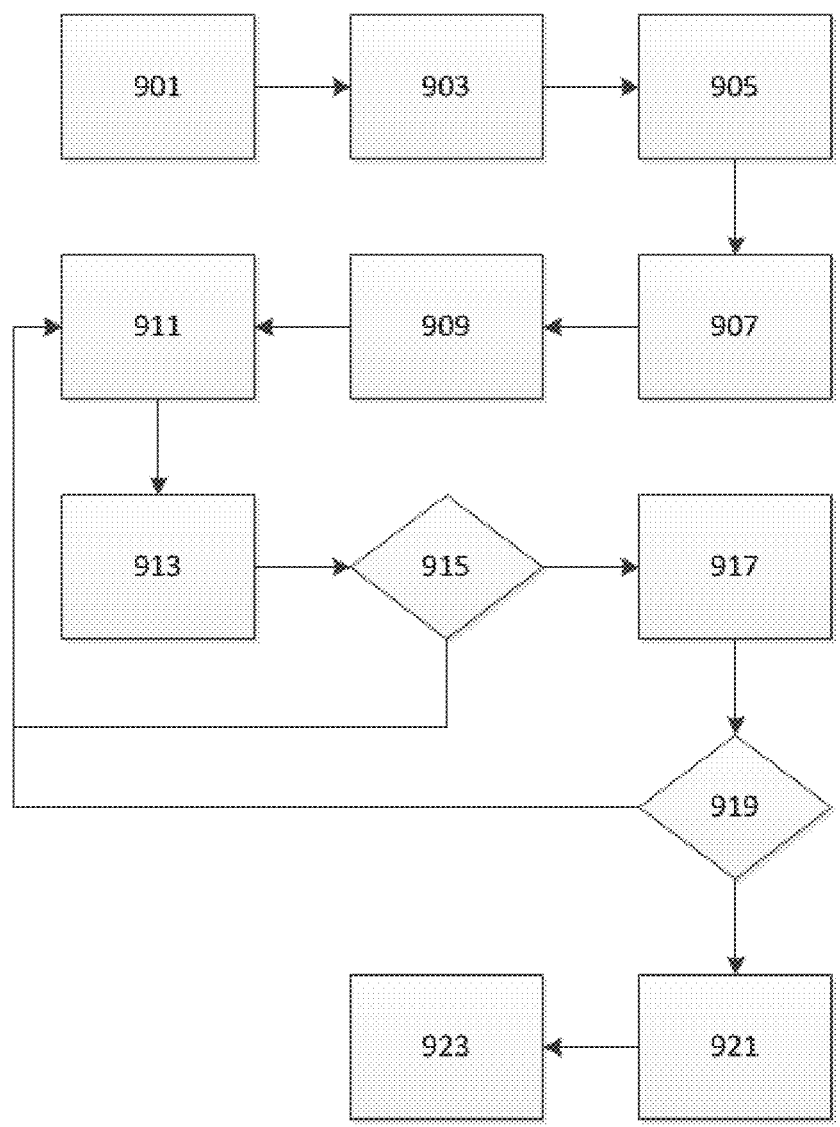
FIG. 9 depicts a flowchart view of a method for monitoring for scale, according to one or more embodiments.

FIG. 9 is a flowchart of an example method 900 of monitoring for scale that can form on equipment, in accordance with one or more embodiments. Not all of the steps of the method 900 must be performed, nor must they be performed in the order presented. Any of these steps may be executed by the processors 309, 320, the processor of the surface control unit 22, or an operator of the nuclear logging tool.

In step 901, the nuclear logging tool 10 is run into the borehole to obtain a gamma ray log at a first time, and the gamma ray detectors 306A-C are responsive to natural gamma ray sources. The gamma ray detectors 306A-C can generate passive gamma ray counts of scale contributors to produce a gamma ray log along the borehole as a function of depth. Optionally, at step 903, the gamma ray measurements of a scale contributor are compared at different locations around or proximate to the equipment undergoing monitoring, such as the pump 30 of FIG. 2. For example, the gamma ray counts of radium at a location above the pump, at the pump, and below the pump are compared. If an increase in radium is observed at the pump compared to one of the other locations, it may indicate that a scale compound with radium as the cation is forming at the pump's location.

In step 905, the neutron source 203 can be activated to irradiate potential scale contributors along the borehole; and the gamma ray detectors 306A-C are responsive to activated gamma rays sources. The gamma ray detectors 306A-C generate active gamma ray counts of scale contributors to produce an active gamma ray log along the borehole as a function of depth. Optionally, at step 907, the gamma ray measurements of a scale contributor are compared at different locations around or proximate to the equipment, such as the pump 30 of FIG. 2. If there is an increase in scale co-contributors at the equipment compared to locations above or below the equipment, a scale compound is identified. It should be understood that the active gamma ray measurements can be collected before the passive and that either active or passive gamma ray measurements can be collected to monitor for scale forming on the equipment.

Figure 10:
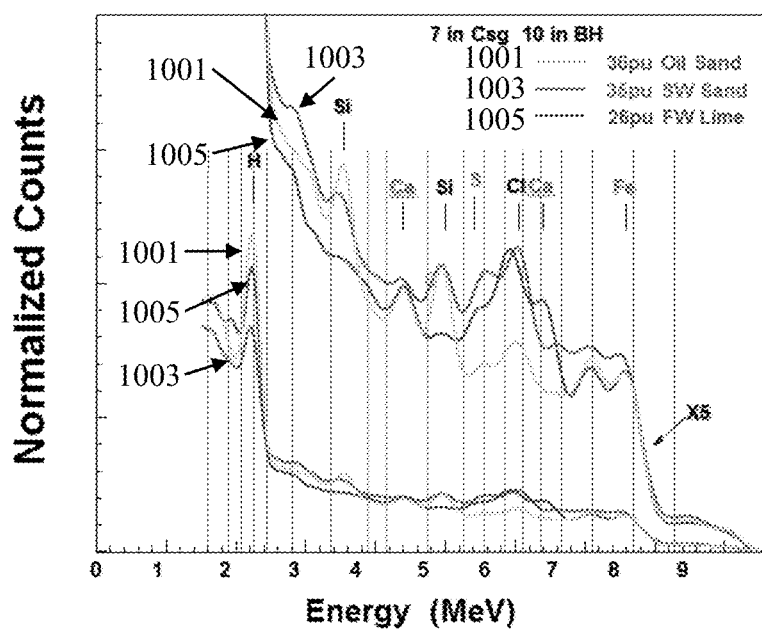
FIG. 10 depicts a graph view of a gamma ray energy spectrum, according to one or more embodiments.

At step 909, by applying the fitting process described herein, the gamma ray logs can be converted to a normalized gamma ray spectrum. FIG. 10 shows a graph view of a normalized gamma ray spectrum generated from a gamma ray log obtained in borehole 12 of FIG. 1, in accordance with one or more embodiments. As shown, curves 1001, 1003, and 1005 are representative of the elemental yields of different formations, oil-sand, salt water sand, and fresh water limestone. In the gamma ray spectrum, peaks attributable to helium, silicon, calcium, sulfur, chlorine, and iron are shown. It should be understood that a similar gamma ray spectrum indicative of the concentration of scale contributors can be generated from the gamma ray counts obtained at steps 901 and 905 and used to identify scale compounds forming on the equipment undergoing monitoring.

Referring to FIG. 9, at step 911, after the gamma ray log is obtained at the first time, an additional gamma ray log is obtained at a second time different from the first (e.g., after 4 weeks, 2 months, or any amount of time when scale deposits might have increased in concentration) and can be converted to a normalized gamma ray spectrum. The second gamma ray log may include passive gamma ray measurements, active gamma ray measurements, or both passive and active gamma ray measurements. At step 913, one or more scale contributors may be identified in the gamma ray spectrums produced from the first and second logs. That is, all the elemental yields are identified using the gamma ray logs, and scale contributors are identified within the elemental yields (e.g., peaks attributable to a scale contributor may be identified).

In step 915, gamma ray counts of a scale contributor (e.g., an element of a cation or anion included in a scale compound) obtained from the first time are compared with gamma ray counts of the same scale contributor from the second time to determine whether there is an increase in the scale contributor at a particular location. For example, suppose at the first time the average gamma ray count of sulfur was about 600 at the location, and then at the second time the average gamma ray count was about 700 at the same location. This increase in concentration of sulfur (which is an element of a common anion, sulfate) may indicate an accumulation of a scale compound at that location. If there is no increase in concentration of a scale contributor, monitoring for scale compounds may continue at step 911.

At step 915, if an increase in concentration of the scale contributor (e.g., sulfur from $RaSO_4$) is observed, the gamma ray measurements for a scale co-contributor within the same scale compound (e.g., radium from $RaSO_4$) is compared between the first and second log times to identify whether there is an increase in concentration of the scale co-contributors (e.g., Ra and S from $RaSO_4$) at a particular location. This increase in co-contributors of a cation and anion is used to identify a scale compound forming at the location. The scale co-contributors may be compared by analyzing the gamma ray spectral graphs (such as the graph depicted in FIG. 10) obtained from the different log times. For example, the peaks attributable to the co-contributors may be compared between gamma ray spectral graphs of the first and second log times. If there is no increase in concentration of scale co-contributors, monitoring for scale compounds may continue at step 911.

The co-contributors compared may between scale co-contributors obtained from a natural gamma ray source and neutron activated gamma ray source (e.g., Ra and S from $RaSO_4$). Optionally, the co-contributors compared may be between two neutron activated gamma ray sources (e.g., Fe and S from $FeS_2$). The scale co-contributors may be compared by plotting the gamma ray counts of the scale co-contributors over time.

Figure 11:
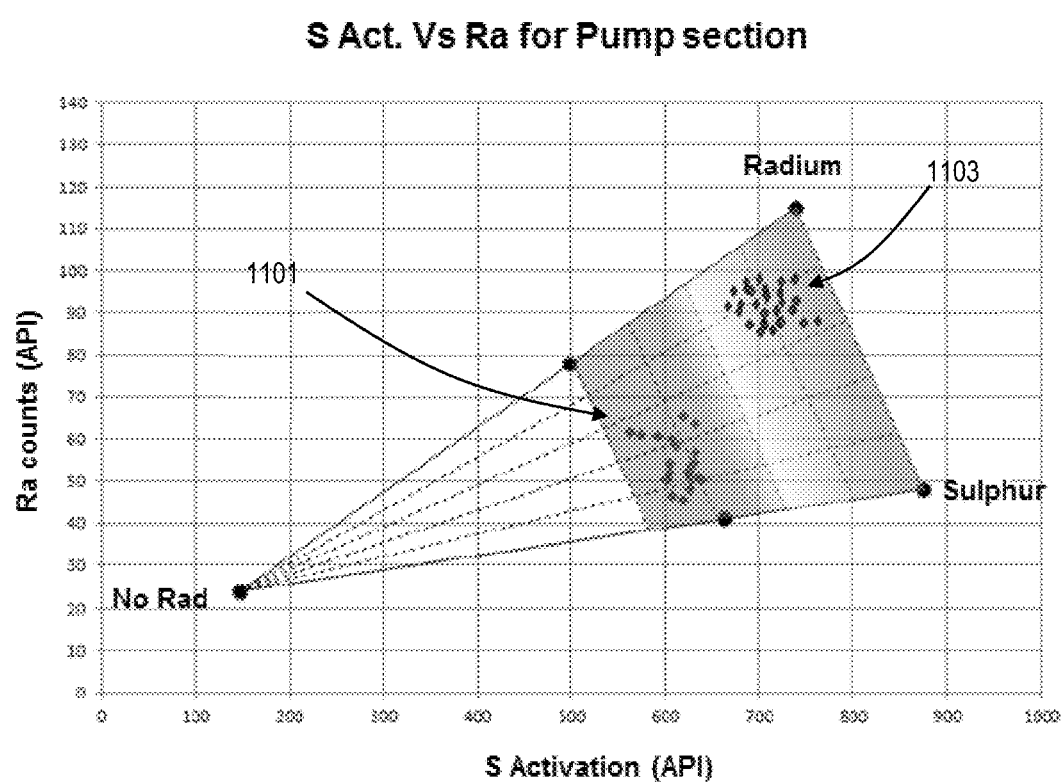
FIG. 11 depicts a graph view of a cross-plot of relative gamma ray counts for scale co-contributors, according to one or more embodiments.

FIG. 11 is a graph view of a plot of scale co-contributors over time, in accordance with one or more embodiments. As shown, the gamma ray counts associated with radium are in the ordinate and the gamma ray counts associated with sulfur are in the abscissa. A cluster of gamma ray counts 1101 were measured at a first time and another cluster of gamma ray counts 1103 were measured after the first time in the same location (e.g., proximate the pump 30 of FIG. 2). This graph indicates that the concentration of radium sulfate ($RaSO_4$) increased between the first and second times and can be used to identify a scale compound forming at the location.

An additional scale co-contributor may be plotted in the graph using the second ordinate. For example, a cross-plot between oxygen and sulfur may be added to the graph illustrated in FIG. 11 by including an axis for oxygen gamma ray counts on the right ordinate. It should be appreciated that two or more scale co-contributors may be compared in a cross-plot or from gamma ray spectral graphs.

Referring to FIG. 9, at step 917, a scale compound is identified by identifying the increase in scale co-contributors in the gamma ray spectra over time. At step 919, it is determined whether the scale buildup on the equipment satisfies a threshold. For example, if one or more scale measurement meets or surpasses a threshold (e.g., above about 700 gamma ray counts for radium), a suitable scale remediation process (e.g., chemical dissolution, jetting, milling, replacing the equipment with scale, or any other suitable scale remediation process) can be selected or determined based on the identified scale compound (921). At step 923, the remediation process may be performed to decrease the scale compound on the equipment undergoing the monitoring. Otherwise, monitoring for scale buildup on the equipment (911) may continue until the scale concentration satisfies the threshold at step 919.

It should be appreciated that the nuclear logging tool 10 may remain in the borehole to obtain gamma ray measurements at the first and second times between steps 901 and 911. Also, the nuclear logging tool 10 may be permanently installed in the borehole or integrated with the equipment installed downhole undergoing the monitoring as described herein. The method described herein is not limited to monitoring for scale compounds in a borehole, but also may be applied to equipment in contact with scale contributors.

In addition to the embodiments described above, many examples of specific combinations are within the scope of the disclosure, some of which are detailed below:

Example 1

A method of monitoring for scale compounds that include scale co-contributors of cations and anions, comprising:
  measuring gamma ray counts of scale contributors using a spectral gamma ray detector; and identifying a scale compound by identifying an increase in scale co-contributors over time.

Example 2

The method of example 1, wherein measuring further comprises:
measuring passive gamma ray counts of scale contributors using a spectral gamma ray detector;
activating a neutron source to produce active gamma ray counts of scale contributors; and
measuring the active gamma ray counts using the spectral gamma ray detector.

Example 3

The method of example 1, further comprising plotting gamma ray counts of the scale co-contributors over time.

Example 4

The method of example 1, further comprising determining a scale remediation process based on the scale compound identified.

Example 5

The method of example 4, further comprising decreasing the scale compound based on the determined scale remediation process.

Example 6

The method of example 1, further comprising identifying a second scale compound by identifying an increase in scale co-contributors for the second scale compound over time.

Example 7

The method of example 1, further comprising monitoring for scale compounds in a pump downhole in a well.

Example 8

The method of example 1, further comprising:
measuring gamma ray counts of scale contributors at a first time to produce a first log;
measuring gamma ray counts of scale contributors at a second time to produce a second log; and
identifying a scale compound by identifying an increase in scale co-contributors from the first log to the second log.

Example 9

The method of example 1, wherein measuring further comprises measuring passive gamma ray counts of scale contributors using a spectral gamma ray detector.

Example 10

The method of example 1, wherein measuring further comprises:
activating a neutron source to produce active gamma ray counts of scale contributors; and
measuring the active gamma ray counts using the spectral gamma ray detector.

Example 11

The method of example 1, wherein identifying the scale compound comprises identifying an increase in a scale contributor and confirming an increase in the scale co-contributor.

Example 12

The method of example 1, further comprising measuring gamma ray counts of scale contributors from a distance away from the scale compound.

Example 13

The method of example 12, further comprising measuring gamma ray counts of scale contributors through a structure.

Example 14

A system for monitoring for scale compounds that include scale co-contributors of cations and anions, comprising:
a nuclear tool, comprising a spectral gamma ray detector responsive to gamma rays emitted from scale contributors; and
a processor configured to:
analyze gamma ray counts of scale contributors generated using the spectral gamma ray detector; and
identify a scale compound by identifying an increase in scale co-contributors over time.

Example 15

The system of example 14, wherein:
the nuclear tool further comprises a neutron source configured to activate scale contributors;
the spectral gamma ray detector is further configured to generate passive and active gamma ray counts of scale contributors; and
the processor is further configured to measure the passive and active gamma ray counts generated from the spectral gamma ray detector.

Example 16

The system of example 14, wherein the processor is further configured to generate a plot of gamma ray counts of the scale co-contributors over time.

Example 17

The system of example 14, wherein the processor is further configured to determine a scale remediation process based on the scale compound identified.

Example 18

The system of example 14, wherein the processor is further configured to identify a second scale compound by identifying an increase in scale co-contributors for the second scale compound over time.

Example 19

The system of example 14, wherein the nuclear tool is configured to monitor for scale compounds in a pump downhole in a well.

Example 20

The system of example 14, wherein:
the spectral gamma ray detector is further configured to:
generate gamma ray counts of scale contributors at a first time to produce a first log; and
generate gamma ray counts of scale contributors at a second time to produce a second log; and
the processor is further configured to identify a scale compound by identifying an increase in scale co-contributors from the first log to the second log.

Example 21

The system of example 14, wherein the spectral gamma ray detector is further configured to generate passive gamma ray counts of scale contributors.

Example 22

The system of example 14, wherein:
the nuclear tool further comprises a neutron source configured to activate scale contributors;
the spectral gamma ray detector is further configured to generate active gamma ray counts of scale contributors; and
the processor is further configured to measure the active gamma ray counts of the scale contributors.

This discussion is directed to various embodiments of the invention. The drawing figures are not necessarily to scale. Certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed may be employed separately or in any suitable combination to produce desired results. In addition, one skilled in the art will understand that the description has broad application, and the discussion of any embodiment is meant only to be exemplary of that embodiment, and not intended to suggest that the scope of the disclosure, including the claims, is limited to that embodiment.

Certain terms are used throughout the description and claims to refer to particular features or components. As one skilled in the art will appreciate, different persons may refer to the same feature or component by different names. This document does not intend to distinguish between components or features that differ in name but not function, unless specifically stated. In the discussion and in the claims, the terms "including" and "comprising" are used in an open-ended fashion, and thus should be interpreted to mean "including, but not limited to . . . ." Also, the term "couple" or "couples" is intended to mean either an indirect or direct connection. In addition, the terms "axial" and "axially" generally mean along or parallel to a central axis (e.g., central axis of a body or a port), while the terms "radial" and "radially" generally mean perpendicular to the central axis. The use of "top," "bottom," "above," "below," and variations of these terms is made for convenience, but does not require any particular orientation of the components.

Reference throughout this specification to "one embodiment," "an embodiment," or similar language means that a particular feature, structure, or characteristic described in connection with the embodiment may be included in at least one embodiment of the present disclosure. Thus, appearances of the phrases "in one embodiment," "in an embodiment," and similar language throughout this specification may, but do not necessarily, all refer to the same embodiment.

Although the present invention has been described with respect to specific details, it is not intended that such details should be regarded as limitations on the scope of the invention, except to the extent that they are included in the accompanying claims.

What is claimed is:

1. A method of monitoring for scale compounds that include scale co-contributors of cations and anions, comprising:
measuring gamma ray counts of scale contributors using a spectral gamma ray detector at a first time to produce a first log;
measuring gamma ray counts of scale contributors using a spectral gamma ray detector at a second time to produce a second log, wherein the second time is separate from the first time and the second time is later than the first time; and
identifying a scale compound by identifying an increase in scale co-contributors from the first log to the second log.

2. The method of claim 1, wherein measuring further comprises:
measuring passive gamma ray counts of scale contributors using a spectral gamma ray detector;
activating a neutron source to produce active gamma ray counts of scale contributors; and
measuring the active gamma ray counts using the spectral gamma ray detector.

3. The method of claim 1, further comprising plotting gamma ray counts of the scale co-contributors over time.

4. The method of claim 1, further comprising determining a scale remediation process based on the scale compound identified.

5. The method of claim 4, further comprising decreasing the scale compound based on the determined scale remediation process.

6. The method of claim 1, further comprising identifying a second scale compound by identifying an increase in scale co-contributors for the second scale compound over time.

7. The method of claim 1, further comprising monitoring for scale compounds in a pump downhole in a well.

8. The method of claim 1, wherein measuring further comprises measuring passive gamma ray counts of scale contributors using a spectral gamma ray detector.

9. The method of claim 1, wherein measuring further comprises:
activating a neutron source to produce active gamma ray counts of scale contributors; and
measuring the active gamma ray counts using the spectral gamma ray detector.

10. The method of claim 1, wherein identifying the scale compound comprises identifying an increase in a scale contributor and confirming an increase in the scale co-contributor.

11. The method of claim 1, further comprising measuring gamma ray counts of scale contributors from a distance away from the scale compound.

12. The method of claim 11, further comprising measuring gamma ray counts of scale contributors through a structure.

13. A system for monitoring for scale compounds that include scale co-contributors of cations and anions, comprising:
- a nuclear tool, comprising a spectral gamma ray detector responsive to gamma rays emitted from scale contributors generate gamma ray counts of scale contributors at a first time to produce a first log; and generate gamma ray counts of scale contributors at a second time to produce a second log, wherein the second time is separate from the first time and the second time is later than the first time; and
- a processor configured to:
  - analyze gamma ray counts of scale contributors generated using the spectral gamma ray detector; and
  - identify a scale compound by identifying an increase in scale co-contributors from the first log to the second log.

14. The system of claim 13, wherein:
- the nuclear tool further comprises a neutron source configured to activate scale contributors;
- the spectral gamma ray detector is further configured to generate passive and active gamma ray counts of scale contributors; and
- the processor is further configured to measure the passive and active gamma ray counts generated from the spectral gamma ray detector.

15. The system of claim 13, wherein the processor is further configured to generate a plot of gamma ray counts of the scale co-contributors over time.

16. The system of claim 13, wherein the processor is further configured to determine a scale remediation process based on the scale compound identified.

17. The system of claim 13, wherein the processor is further configured to identify a second scale compound by identifying an increase in scale co-contributors for the second scale compound over time.

18. The system of claim 13, wherein the nuclear tool is configured to monitor for scale compounds in a pump downhole in a well.

19. The system of claim 13, wherein the spectral gamma ray detector is further configured to generate passive gamma ray counts of scale contributors.

20. The system of claim 13, wherein:
- the nuclear tool further comprises a neutron source configured to activate scale contributors;
- the spectral gamma ray detector is further configured to generate active gamma ray counts of scale contributors; and
- the processor is further configured to measure the active gamma ray counts of the scale contributors.

* * * * *